(12) United States Patent
Berthonnaud et al.

(10) Patent No.: US 7,955,279 A0
(45) Date of Patent: Jun. 7, 2011

(54) DEVICE FOR EVALUATING A POSITION OF BALANCE FOR THE HUMAN BODY

(75) Inventors: Eric Berthonnaud, Charbonnieres les Bains (FR); Joannès Dimnet, Caluire et Cuire (FR); Pierre Roussouly, Saint Cyr Au Mont d'Or (FR)

(73) Assignee: SDGI Holdings, Inc., Wilmington, DE (US)

( * ) Notice: Subject to any disclaimer, the term of this patent is extended or adjusted under 35 U.S.C. 154(b) by 2440 days.

(21) Appl. No.: 10/169,783

(22) PCT Filed: Jan. 10, 2001

(86) PCT No.: PCT/FR01/00060

§ 371 (c)(1), (2), (4) Date: Jul. 3, 2002

(87) PCT Pub. No.: WO01/50956

PCT Pub. Date: Jul. 19, 2001

(65) Prior Publication Data

US 2003/0004438 A1 Jan. 2, 2003

(30) Foreign Application Priority Data

Jan. 10, 2000 (FR) ...................................... 00 00497

(51) Int. Cl.
*A61B 5/103* (2006.01)

(52) U.S. Cl. ......................... 600/595; 600/587; 382/132
(58) Field of Classification Search .................. 600/587, 600/595, 407, 436, 425; 382/128, 132; 378/207, 378/18, 62
See application file for complete search history.

(56) References Cited

U.S. PATENT DOCUMENTS

| | | | |
|---|---|---|---|
| 5,080,109 A * | 1/1992 | Arme, Jr. ...................... | 600/595 |
| 5,609,162 A | 3/1997 | Blumentritt et al. | |
| 6,282,306 B1 * | 8/2001 | Inoue et al. .................... | 382/132 |
| 6,434,415 B1 * | 8/2002 | Foley et al. .................... | 600/425 |

FOREIGN PATENT DOCUMENTS

| | | | |
|---|---|---|---|
| EP | 0119660 | | 9/1984 |
| GB | 2186375 A | * | 8/1987 |
| NL | 7415910 | | 6/1976 |

* cited by examiner

*Primary Examiner* — Charles Marmor
(74) *Attorney, Agent, or Firm* — Haynes and Boone, LLP

(57) ABSTRACT

According to the invention, the patient (4) is placed upon a patient support (3) between an X-ray source (1) and a support for the target plate (2) sensitive to the X-rays. The patient support (3) is connected to a device for detecting the horizontal position of the global axis of gravity (5) of the patient when the X-ray source (1) is in operation. The patient (4) can, for example, remain standing. The inventive device can superimpose an image (Hg) of the global axis of gravity (5) on the digital radiographic image of the patient (4).

10 Claims, 4 Drawing Sheets

DEVICE FOR EVALUATING A POSITION OF BALANCE FOR THE HUMAN BODY

TECHNICAL FIELD OF THE INVENTION

The present invention concerns a device for evaluating an equilibrium position of the human body, in particular an equilibrium position of the spinal column.

The diagnosis of back pain is generally based on interpreting one or more radiographic images, produced by a machine including a source of X-rays, support means for a target plate sensitive to X-rays, and patient support means adapted to support a patient in a fixed position between the source of X-rays and the target plate support means. The practitioner must interpret the radiographic images to deduce therefrom the probable causes of the patient's back pain.

Analyzing radiographic images is difficult, and despite the great experience of practitioners, this analysis does not take sufficiently reliable and complete account of the causes of some spinal afflictions. In some cases, the radiographic images lead to diagnostic errors.

To effect a more comprehensive analysis of the human skeleton, with the aim of understanding better the origin of some back pains afflicting patients, the documents NL 7 415 910 A and EP 0 119 660 A have already proposed marking the vertical axis passing through the center of gravity of the patient automatically on a radiographic image of the spinal column. To this end a system described in these documents includes a source of X-rays, means for supporting a target plate sensitive to X-rays, patient support means adapted to support a patient in a fixed position between the source of X-rays and the target plate support means, and means associated with the patient support means to detect the horizontal position of the global axis of gravity of the patient during operation of the source of X-rays and to generate position signals. The position signals control a top carriage moving transversely and supporting a vertical plumbline placed between the patient and the support for the target plate sensitive to X-rays, with the aim of aligning the plumbline with the source of X-rays and the global axis of gravity. In this way the position of the global axis of gravity of the patient can be seen in the radiographic image, characterizing the equilibrium of the patient.

The above kind of device nevertheless has a number of drawbacks that prevent its effective use in practice. First of all, the precision and reliability of the position of the global axis of gravity in the radiographic image are unsatisfactory. Most importantly, the mechanical system with a mobile carriage and a vertical plumbline is a nuisance and a source of errors because of its bulkiness, the risks of the plumbline snagging, and the attention that must necessarily be paid to the time of movement of the plumbline support carriage.

Another drawback results generally from the variable and uncontrolled position of the patient on the patient support means, which degrades the readability of the radiographic image.

SUMMARY OF THE INVENTION

The problem addressed by the present invention is that of designing a new system avoiding the drawbacks of prior art systems, in particular by eliminating all sources of nuisance and errors that can stem from the use of a mobile vertical plumbline, and by making totally transparent to the user the transfer of the position of the global axis of gravity of the patient onto the radiographic image.

Another problem addressed by the invention is that of improving the accuracy and reliability of the radiographic images obtained in this way, to enable high-resolution interpretation of the position of the global axis of gravity relative to the skeleton of the patient.

To achieve the above and other objects, the invention provides a system for evaluating an equilibrium position of the human body, including a source of X-rays and means for supporting a target plate sensitive to X-rays to produce on the target plate a radiographic image of the patient, and patient support means for supporting a patient in a fixed position between the source of X-rays and the support means for the target plate and for generating position signals imaging the horizontal position of the global axis of gravity of the patient relative to the source of X-rays and the target plate;

The system according to the invention includes:
   scanning means for digitizing the radiographic image of the patient produced on the target plate, and thereby generating a digitized image,
   means for generating, as a function of said position signals, a digitized image of the cast shadow of the global axis of gravity in the plane of the target plate,
   means for combining with said digitized radiographic image of the patient the digitized image of the cast shadow of the global axis of gravity, and thereby generating a combined digitized image,
   and means for viewing said combined digitized image.

The image is therefore produced by electronic means situated entirely outside the space occupied by the patient when taking the radiographic image, and totally insensitive to the risks of being displaced by movements of the patient. Moreover, the accuracy of the image obtained in this way is significantly improved, since plumbline position errors are entirely eliminated.

In one practical embodiment, the means for generating a digitized image of the cast shadow of the global axis of gravity include:
   a calculation unit and an associated memory,
   geometrical data, stored in the memory, and corresponding to the relative positions of the source of X-rays, the plane of the sensitive plate, and the patient support means in a fixed system of axes,
   a program stored in a program memory area of the memory for storing said position signals at the time of taking the radiographic image, calculating, as a function of said position signals, the straight line segment intersecting the plane of the sensitive plate and the vertical plane passing through the source of X-rays and the horizontal position of the global axis of gravity, and storing the result of this calculation, which constitutes the image of the global axis of gravity.

The system is preferably such that:
   it includes a scanner for scanning the radiographic image produced on the target plate sensitive to X-rays and producing a series of digital signals constituting the digitized radiographic image,
   the program is adapted to receive said digital signals and stores them in the memory,
   the program is adapted to modify the stored digitized radiographic image by substituting the image of the global axis of gravity, thereby generating said combined digitized image,
   and the program is adapted to display said combined digitized image on a monitor or prints it out on a support.

In a preferred embodiment, further improving accuracy, the program includes a calibration sequence, adapted for scanning the radiographic image of a calibration object with radio-opaque markers, and calculating said geometrical data from known positions and dimensions of the radio-opaque markers of said calibration object, and storing the data in the memory. This solves the problem of uncertainty related to the unknown position of the source of X-rays, which is generally incorporated into an X-ray head whose interior cannot be seen. By positioning the calibration object appropriately and in a marked way on the patient support means, and taking a radiographic image of the calibration object when so positioned, all the geometrical data necessary, i.e. the relative positions of the source, the patient support means and the target plate, is determined in one operation, enabling subsequent accurate calculation of the position of the image of the global axis of gravity relative to the radiographic image of the bones of the patient.

One cause of the lack of accuracy and reliability of prior art systems that include a force plate for detecting the horizontal position of the global axis of gravity of the patient is the possibility of drift in the specifications of the force plate sensors. As a result of such drift, the signals produced by each of the sensors can vary in time, which leads to an erroneous determination of the position of the global axis of gravity. The invention solves this problem by providing a calibration weight and a calibration sequence to be effected periodically. The calibration weight, which is removable and can be positioned on the patient support means, has a particular shape, position marker means which can be made to coincide with complementary marker means on the patient support means, and a center of gravity whose position relative to the position marker means is known. The calibration sequence, provided in the stored program, is adapted to calculate correction parameters for the force signals produced by each sensor, so as to make the calculated center of gravity coincide with the known geometrical position of the real center of gravity of the calibration weight. The correction parameters are then stored in memory for subsequent reliable calculation of the position of the global axis of gravity of the patients.

To improve accuracy, the fixed system of axes preferably has its center in the vertical plane passing through the source of X-rays and perpendicular to the support means for the target plate sensitive to X-rays.

The patient support means preferably include armrests on which the patient can rest his arms in a defined advanced position.

In one advantageous embodiment, the patient support means are rotatable about a median vertical axis to orient the patient angularly relative to the direction between the source of X-rays and the support means for the target plate.

In one preferred embodiment, the armrests are attached to a turntable which itself carries a modified weighing machine force plate on a plurality of force sensors distributed at marked positions relative to the system of axes and producing force signals used as position signals by the calculation unit and the program.

The system preferably includes means for indexing selectively the angular position of the patient support means at least every 45°.

BRIEF DESCRIPTION OF THE DRAWINGS

Other objects, features and advantages of the present invention will emerge from the following description of particular embodiments of the invention, which is given with reference to the accompanying drawings, in which.

DESCRIPTION OF THE PREFERRED EMBODIMENTS

Figure 1:
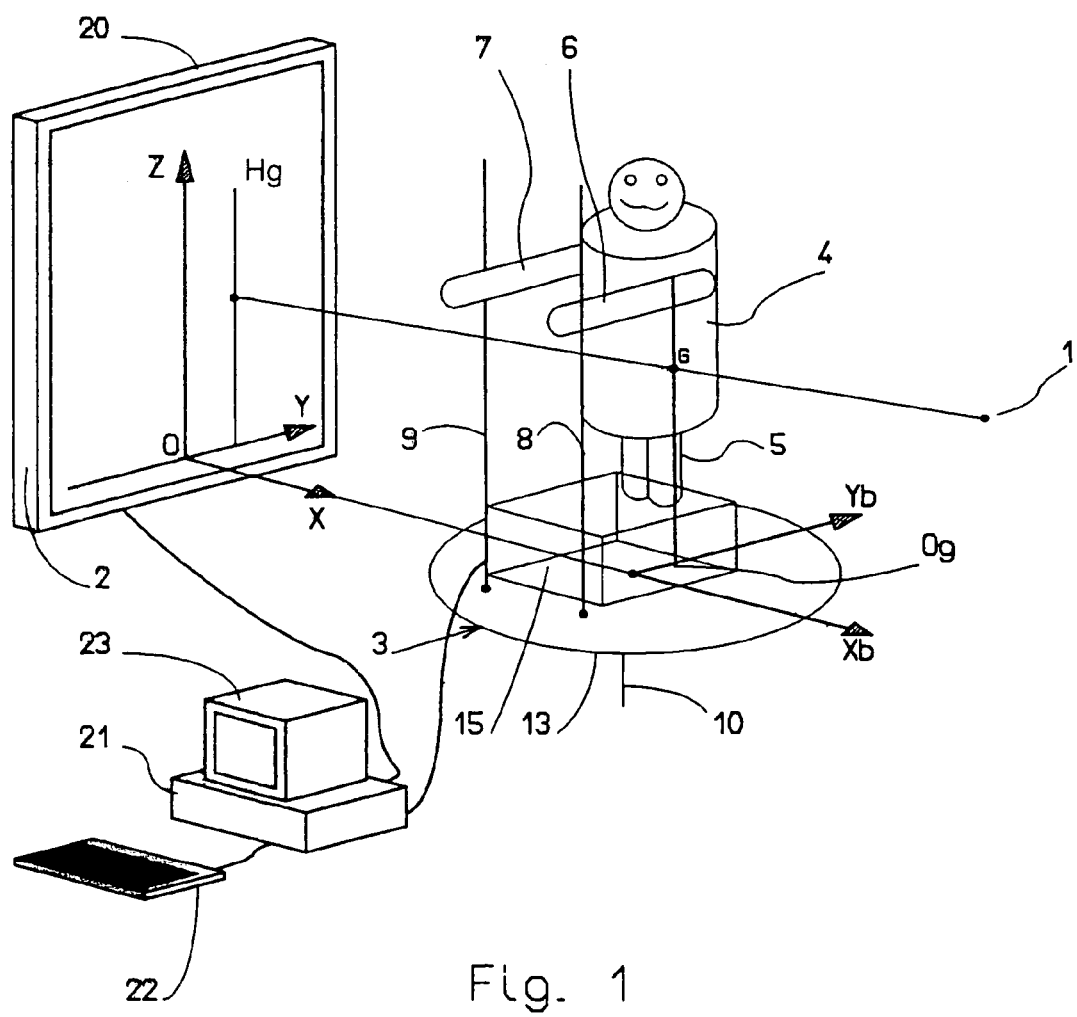
FIG. 1 shows diagrammatically and in perspective an evaluation system conforming to one embodiment of the present invention.
Figure 3:
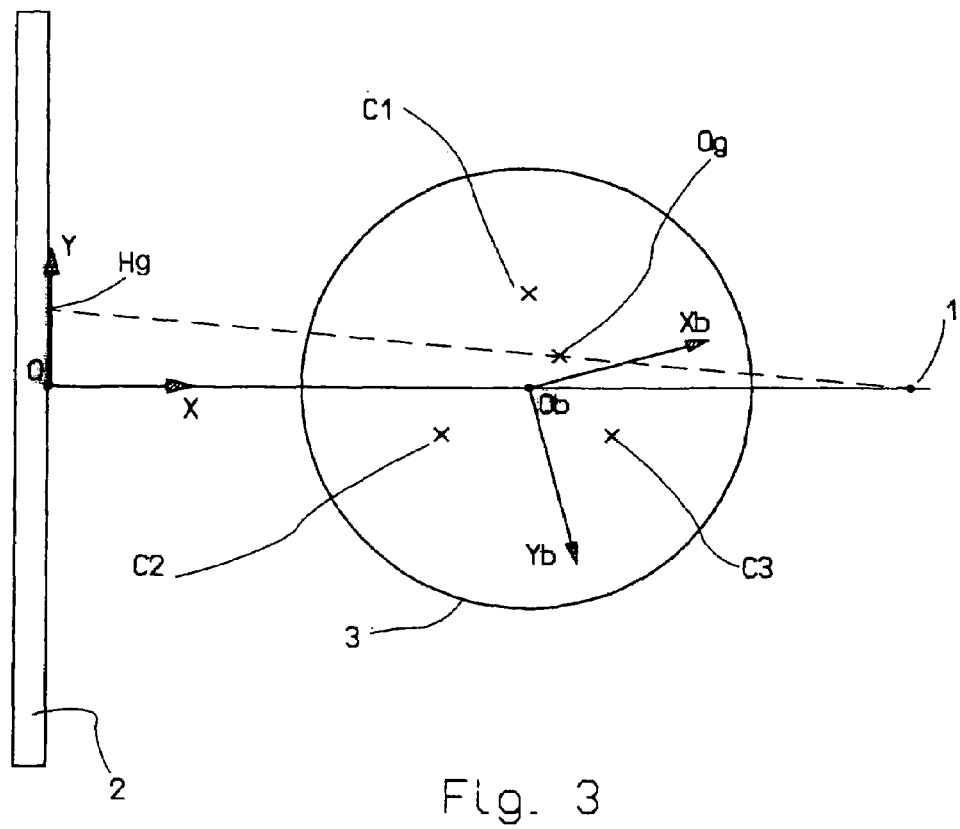
FIG. 3 is a plan view of the evaluation system from FIG. 1.

In the embodiment of the system shown in FIGS. 1 and 3, the system includes a source 1 of X-rays, support means for supporting a target plate 2 sensitive to X-rays and oriented vertically at a particular horizontal distance from the source 1 of X-rays, and patient support means 3 adapted to support a patient 4 in a fixed position between the source 1 of X-rays and the support means for the target plate 2. The system according to the invention is an installation for taking radiographic images. In other words, the source 1 of X-rays, and the support means for the target plate 2 can have a structure like those habitually used in medical radiographic image installations.

In accordance with the invention, the patient support means 3 include means for detecting the horizontal position of the global axis of gravity 5 of the patient 4 (the vertical axis passing through the center of gravity G of the patient), i.e. its coordinates in the horizontal plane, during operation of the source 1 of X-rays.

A priori, the invention can be applied to analyzing the equilibrium of patients 4 in diverse positions such as the standing position or the seated position, for example. FIG. 1 shows an embodiment of the system according to the invention in which the patient support means 3, the source 1 of X-rays and the support means for the target plate 2 produce a radiographic image and simultaneously identify the global axis of gravity 5 of a standing patient 4.

For analyzing the spinal column, the system is adapted to take a radiographic image of the thoracic area, the lumbar area, the pelvic area and the upper femoral area of the patient 4 in the standing position.

In the embodiment in which the patient 4 is standing, it is important for the arms 6 and 7 of the patient to have a constant defined position, because their position affects that of the center of gravity G and the quality of the radiographic image obtained. For example, as shown in the figure, the patient supporting means 3 include armrests 8 and 9, for example vertical rods, on which the patient 4 can rest his arms 6 and 7 in an advanced position, for example in a horizontal position, gripping the rods 8 and 9 with his hands.

The patient support means 3 are preferably rotatable about a median vertical axis 10, enabling the patient 4 to be oriented angularly relative to the direction of propagation of rays between the source 1 of X-rays and the support means for the target plate 2, with several successive angular positions in which a plurality of radiographic images can be taken, for example from the front and then from the side. Indexing means selectively fix the angular position of the patient support means 3 with respect to the median vertical axis 10 in at least eight positions spaced by 45°.

Figure 2:
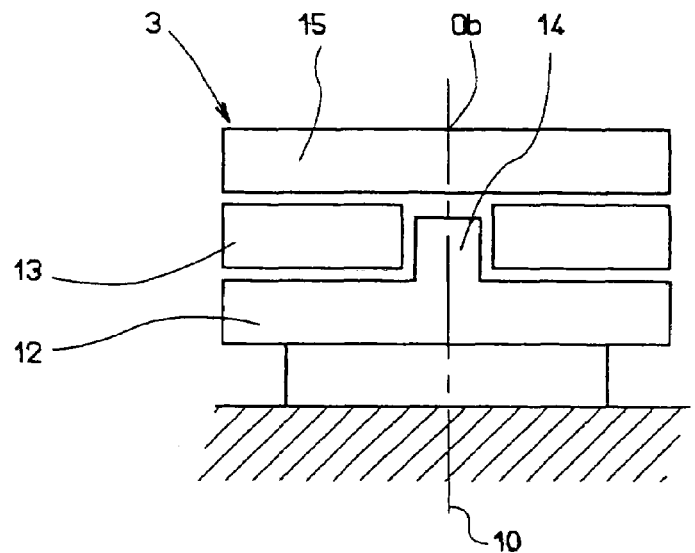
FIG. 2 is a front view in diametral section of patient support means of the FIG. 1 evaluation system.

In the advantageous embodiment shown in FIGS. 2 and 3, the patient 4 rests on patient support means 3 including a modified weighing machine force plate 15 which is provided with a plurality of force sensors such as the sensors C1, C2 and C3, arranged in positions that are marked relative to a system of axes XbObYb, and associated with calculating means for calculating the position Og, in the horizontal plane, of the resultant of the forces in said system of axes XbObYb. More than three sensors can naturally be provided.

The system of axes XbObYb can advantageously have its center Ob in the vertical plane XOZ passing through the source 1 of X-rays and perpendicular to the support means for a target plate 2 sensitive to X-rays.

For example, as shown from the front and in section in FIG. 2, the patient support means 3 include a fixed plate 12, which can be fixed to the floor, on which is mounted a turntable 13 journalled on a top pivot 14 of the fixed plate 12. Thus the top pivot 14 defines the rotation axis of the turntable 13, which is also the median vertical axis 10 of the patient support means 3.

The turntable 13 carries a modified weighing machine force plate 15, which constitutes the surface supporting the patient during operation of the evaluation system according to the invention. The modified weighing machine force plate 15 can be disc-shaped, for example, as shown in FIG. 3.

The modified weighing machine force plate 15 is connected to the turntable 13 by at least three force sensors C1, C2 and C3, adapted to evaluate the vertical bearing force between the modified weighing machine force plate 15 and the turntable 13. As shown in FIG. 3, for example, the force sensors C1, C2 and C3 are equidistantly spaced at 120° from each other around the center Ob.

Vertical forces F1, F2 and F3 act on the three sensors C1, C2 and C3.

The barycenter of the locations of the sensors C1, C2 and C3 assigned the coefficients F1, F2 and F3 is the point $O_g$ at which the global axis of gravity 5 of the patient intersects the bearing plane. This point $O_g$ is determined by elementary calculations from known coordinates of the positions of the sensors C1, C2 and C3 and measured values of the forces F1, F2 and F3. The calculation applies the equation:

$$F1.\overrightarrow{ObC1}+F2.\overrightarrow{ObC2}+F3.\overrightarrow{ObC3}=(F1+F2+F3).\overrightarrow{ObOg}$$

The above calculation can be carried out by an appropriately programmed microcontroller integrated into the modified weighing machine force plate 15, or located somewhere else, as will be evident to the person skilled in the art.

As shown in FIG. 1, a calculation unit 21 and an associated memory are preferably provided, for example a microcomputer and the usual peripheral devices, such as a keyboard 22 and a monitor 23. The calculation unit 21 is electrically connected to the patient support means 3 to receive position signals generated by the patient support means 3 and to calculate the coordinates of the point Og.

According to the invention, scanning means are provided for digitizing the radiographic image of the patient on the support means for the target plate 2. A scanner 20 adapted to scan the radiographic image produced on the target plate 2 sensitive to X-rays can be used for this purpose, and to produce a series of digital signals constituting the digitized radiographic image. In accordance with the invention, calculation and image processing means are further provided for superimposing the digitized image Hg of the global axis of gravity 5 in the vertical plane of the plate sensitive to X-rays on said digitized image of the patient.

The calculation means are preferably associated with memory means for storing coordinates of the position Og of the resultant of the forces on the modified weighing machine force plate 15 at the moment the radiographic image is taken. Accordingly, the relative position of the radiographic image of the patient and the image Hg of the global axis of gravity 5 correspond exactly, allowing for the inherent enlargement that results from the principle of radiography, at the relative position of the skeleton of the patient 4 and the position of his global axis of gravity 5 in the defined attitude in which the radiographic image is taken.

Figure 5:
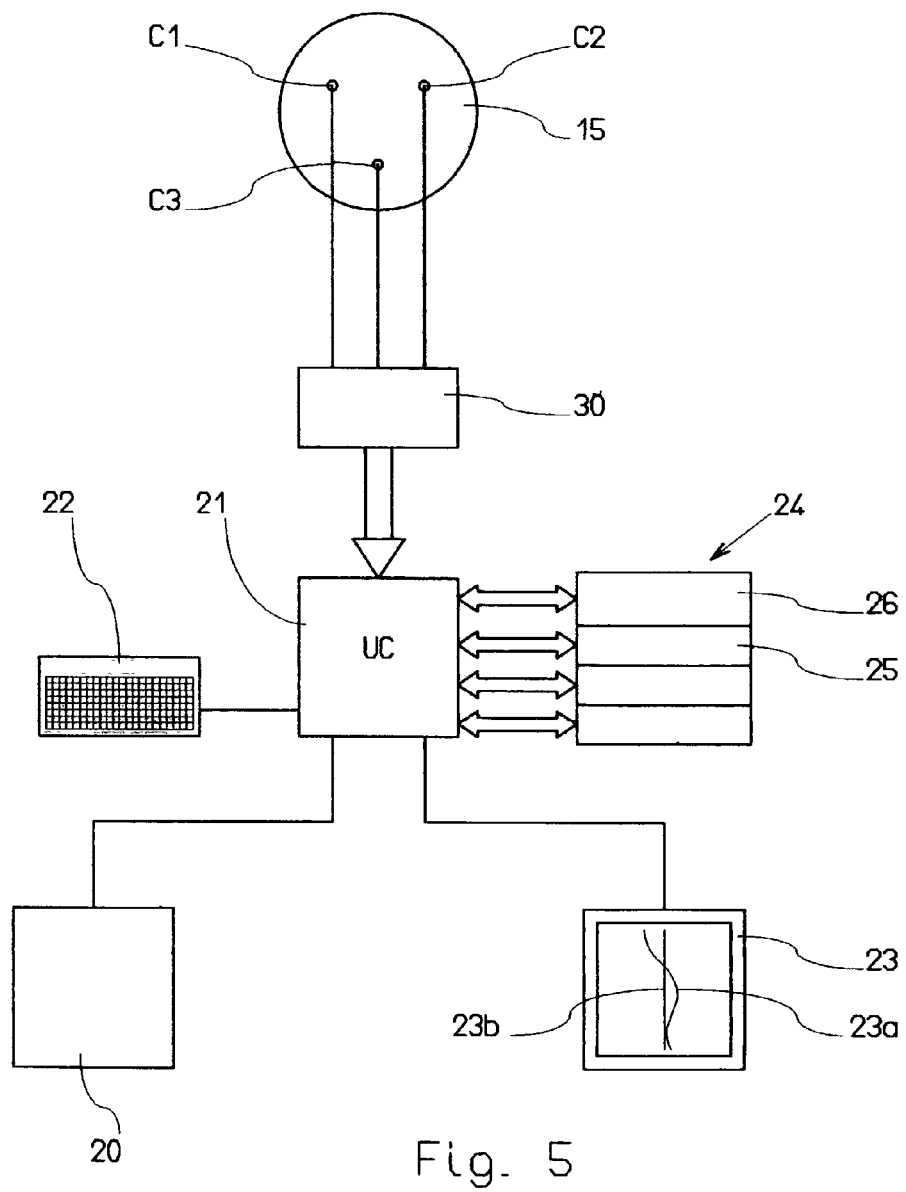
FIG. 5 is a simplified block diagram showing the essential hardware and software for carrying out the calculations that generate images in accordance with the invention.

FIG. 5 is a more detailed diagram of the calculations and image generation means.

It shows the calculation unit 21 such as the central processor unit of a microcomputer or a microprocessor, associated with its peripheral devices such as the keyboard 22 and the monitor 23. The position signals generated by the force sensors C1, C2 and C3 are sent to the calculation unit 21 via an analog/digital converter 30. The calculation unit 21 carries out the calculation previously mentioned to deduce therefrom the coordinates of the global axis of gravity 5 in the fixed horizontal system of axes XbObYb i.e. the position of the point Og. These coordinates are stored in a data memory area 25 of the memory 24, which is itself connected to the calculation unit 21.

The data memory area 25 further contains other geometrical data corresponding to the relative positions in the system of axes XbObYb of the source 1 of the X-rays, the plane of the target plate 2, and the patient support means 3.

A program is stored in a program memory area 26 of the memory 24. The program is adapted to store said position signals at the time the radiographic image is taken, which time is communicated to the calculation unit 21 via an input connected to the radiographic image apparatus. The program calculates, as a function of said position signals or coordinates of the point Og, the straight line segment Hg intersecting the plane of target plate 2 and the vertical plane passing through the source 1 of X-rays and the horizontal position Og of the global axis of gravity 5. The calculation result is stored in memory 24, and this calculation result constitutes the image of the global axis of gravity 5.

Simultaneously, or later, the scanner 20 scans the radiographic image produced on the target plate 2 sensitive to X-rays, and produces a series of digital signals constituting the digitized radiographic image. The program sends these digital signals to the calculation unit 21 where they are stored in the memory 24.

The program is also adapted to modify the digitized radiographic image stored in the memory 24 by substituting points in the image corresponding to the image of the global axis of gravity Hg, so as to generate a combined digitized image.

Finally, the program is adapted to display said combined digitized image on the monitor 23 or prints it out on a support. The combined digitized image including the digitized radiographic image 23a and the image 23b of the global axis of gravity is therefore shown diagrammatically on the monitor 23.

In practice, it is not rare for there to be some displacement between the source 1 of X-rays and the target plate support 2, or for the exact position of the source 1 of X-rays not to be known accurately, as it is generally hidden inside an X-ray head. It is then not possible to calculate accurately the exact position of the image Hg of the global axis of gravity 5.

To solve this problem, calibration means described below can be provided.

Figure 4:
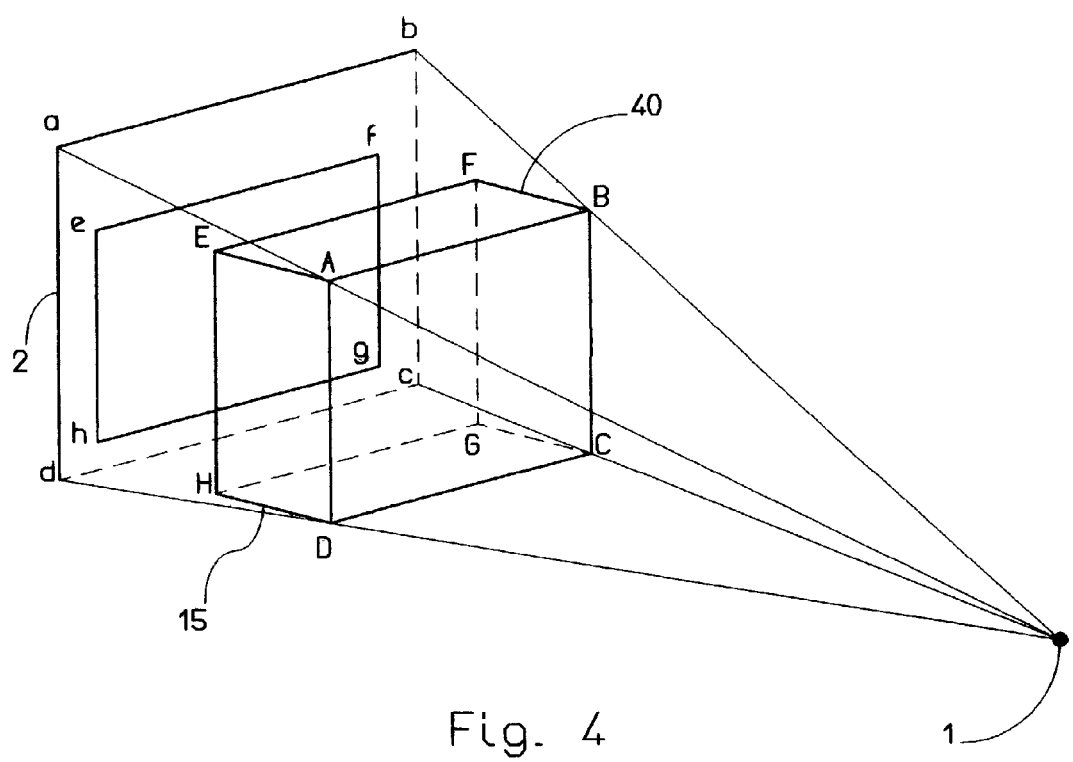
FIG. 4 is a perspective view showing the calibration step using a calibration object.

As shown in FIG. 4, the calibration is effected during a calibration sequence in which a radiographic image of a calibration object 40 with known dimensions and a particular structure and placed in a marked and appropriate position on the patient support means 3 is produced. The calibration object 40 is advantageously a radiotransparent plastics material parallelepiped, with dimensions of 180 mm×180 mm×300 mm, for example, with eight 3 mm diameter radio-opaque lead balls implanted at the vertices. The calibration object 40 carries markings on its bottom base which are made to coincide graphically with corresponding markings on the patient support means 3.

The calibration object is X-rayed under the same conditions as the patient, as shown in FIG. 4, by placing a target plate 2 in the same position as the radiographic image to be made subsequently.

The radiographic image obtained is then digitized with the scanner 20, and the program includes a sequence adapted to recognize the round shapes constituting the images of the balls in the calibration object 40. For example, for a parallelepiped having balls at its eight vertices A, B, C, D, E, F, G and H, an image abcd is obtained of the front face, and a smaller image efgh of the rear face.

The three coordinates of the source 1 of X-rays relative to the fixed system of axes XbObYb are unknown, as are the three coordinates of the center of the calibration object 40 relative to the fixed system of axes, and two angular parameters representing the possible inclinations of the calibration object 40 relative to the system of axes XbObYb. To these eight unknowns there correspond the sixteen measured coordinates of the eight images abcd, efgh of the balls. The program measures the coordinates of these points abcdefgh on the digitized image. A digital technique that will be evident to the person skilled in the art is used to solve the system of sixteen equations in eight unknowns. The redundancy, due to the greater number of equations than unknowns, is used to improve the accuracy of the calculations. The program therefore deduces geometrical data that is then stored in the data memory area 25 of the memory 24.

In practice, it is not rare for the technical specifications of the force sensors C1, C2 and C3, which are electronic sensors generating electrical signals, to drift in time and produce force signals whose processing can no longer reproduce the exact position of the global axis of gravity of patients.

Accordingly, in the situation where the patient support means include a patient support force platform carried by a plurality of force sensors, the system can advantageously be recalibrated periodically using a calibration weight and a calibration sequence.

The calibration weight is a removable weight that can be positioned on the patient support means 3. The calibration weight has a particular shape, for example a parallelepiped-shape like the calibration object 40, or a cylindrical shape, and has a center of gravity whose geometrical position within the volume of the calibration weight is known. The calibration weight includes position marker means, for example on its lower face, which marker means are made to coincide with complementary marker means on the patient support means 3. Accordingly, the geometrical position of the center of gravity of the calibration weight relative to the patient support means 3, and therefore relative to the fixed system of axes XbObYb, is known.

The program stored in the memory includes a calibration sequence which calculates correction parameters for force signals produced by the sensors C1, C2 and C3 in order to make the calculated center of gravity coincide with the known geometrical position of the real center of gravity of the calibration weight. The correction parameters are then stored in memory, to enable reliable subsequent calculation of the position of the global axis of gravity of patients.

Clearly the system according to the invention provides a better understanding of the sagittal equilibrium mechanism. The risks of error are minimized because the system produces the relative position of the global axis of gravity 5 and the human skeleton automatically and accurately.

The embodiment of the invention for making radiographic images in the standing position takes the lower limbs into account, and provides an improved interpretation of defects in the curvature of the spinal column.

Using the radiographic image combined with the image Hg of the global axis of gravity 5, the practitioner can measure the distance between the global axis of gravity 5 and the axis of the heads of the femurs. He can also identify the centers of the heads of the femurs to evaluate the anterior-posterior offset between the global axis of gravity 5 and the heads of the femurs.

After an operator makes specific marks on the radiographic image with the aid of an appropriately programmed computer, the system can reconstruct a spinal and pelvic model for improved characterization and evaluation of the curvatures of the various sections of the spinal column.

The present invention is not limited to the embodiments explicitly described, but includes variants and generalizations thereof within the scope of the following claims.

What is claimed is:

1. A system for evaluating an equilibrium position of the human body, including a source of X-rays, means for supporting a target plate sensitive to X-rays to produce on the target plate a radiographic image of a patient, and patient support means for supporting the patient in a fixed position between the source of X-rays and the support means for the target plate and for generating position signals imaging the horizontal position of the global axis of gravity of the patient relative to the source of X-rays and the target plate, the system including:
   a) scanning means which digitize the radiographic image of the patient produced on the target plate, and which thereby generate a digitized radiographic image,
   b) means for generating, as a function of said position signals, a digitized image of the cast shadow of the global axis of gravity in the plane of the target plate,
   c) means for combining with said digitized radiographic image of the patient the digitized image of the cast shadow of the global axis of gravity for generating a combined digitized image, and
   d) means for viewing said combined digitized image
   wherein the means for generating a digitized image of the cast shadow of the global axis of gravity include:
   e) a calculation unit and an associated memory in which geometrical data are stored corresponding to the relative positions of the source of X-rays, the plane of the target plate, and the patient support means in a fixed system of axes, and
   f) a program stored in a program memory area of the memory, the program adapted for instructing the calculation unit to store said position signals at the time of taking the radiographic image, to calculate, as a function of said position signals, the straight line segment intersecting the plane of the target plate and the vertical plane passing through the source of X-rays and the horizontal position of the global axis of gravity, and to store the result of this calculation, which constitutes the image of the global axis of gravity.

2. A system according to claim 1, wherein:
   the scanning means includes a scanner for scanning the radiographic image produced on the target plate sensitive to X-rays and producing a series of digital signals constituting the digitized radiographic image,
   the program is adapted to instruct the calculation unit to receive said digital signals and stores them in the memory, the program is adapted to provide the means for combining by instructing the calculation unit to modify the stored digitized radiographic image by substituting the image of the global axis of gravity, thereby generating said combined digitized image, and the program is adapted to provide the means for viewing by instructing the calculation unit to display said combined digitized image on a monitor, or print it out on a support.

3. A system according to claim 1, wherein the program includes a calibration sequence, adapted for instructing the calculation unit to scan the radiographic image of a calibration object with radio-opaque markers, and calculate said geometrical data from known positions and dimensions of the radio-opaque markers of said calibration object, and store the data in the memory.

4. A system according to claim 1, wherein the system includes:
  a) the patient support means having a modified weighing machine force plate carried by a plurality of sensors arranged at marked positions relative to the system of axes and producing force signals used by the calculation unit and the program as position signals,
  b) a removable calibration weight which can be positioned on the patient support means, has a particular shape, has a first means for marking position which can be made to coincide with a second means for marking position on the patient support means, and has a center of gravity whose position relative to the first means for marking position is known,
  c) the stored program includes a calibration sequence that instructs the calculation unit to calculate correction parameters for force signals produced by each sensor to make the calculated center of gravity coincide with the known geometrical position of the real center of gravity of the calibration weight, and store the parameters in memory for subsequent reliable calculation of the position of the global axis of gravity of patients.

5. A system according to claim 1, wherein said fixed system of axes has its center in the vertical plane passing through the source of X-rays and perpendicular to the support means for the target plate sensitive to X-rays.

6. A system according to claim 1, adapted to take a radiographic image of the thoracic area, the lumbar area, the pelvic area and the upper femoral area of the patient.

7. A system according to claim 1, wherein the patient support means are rotatable about a median vertical axis to orient the patient angularly relative to the direction of propagation of rays between the source of X-rays and the support means for the target plate.

8. A system according to claim 7, wherein the patient support means include armrests on which the patient can rest his arms in a defined advanced position.

9. The system according to claim 8, wherein the armrests are attached to a turntable which carries a modified weighing machine force plate on a plurality of force sensors distributed at marked positions relative to the system of axes and producing force signals used as position signals by the calculation unit and the program.

10. A system according to claim 7, including means for indexing the angular position of the patient support means at least every 45°.

* * * * *